US007659091B2

(12) United States Patent
Elgebaly

(10) Patent No.: US 7,659,091 B2
(45) Date of Patent: Feb. 9, 2010

(54) DIAGNOSTIC MARKER

(75) Inventor: Salwa A. Elgebaly, Edgewater, MD (US)

(73) Assignee: Nourheart, Inc., Edgewood, MD (US)

( * ) Notice: Subject to any disclaimer, the term of this patent is extended or adjusted under 35 U.S.C. 154(b) by 539 days.

(21) Appl. No.: 10/945,442

(22) Filed: Sep. 21, 2004

(65) Prior Publication Data

US 2006/0063198 A1    Mar. 23, 2006

(51) Int. Cl.
*C12N 15/00* (2006.01)
*A61K 38/04* (2006.01)
(52) U.S. Cl. ........................ 435/69.1; 435/326; 530/324
(58) Field of Classification Search .................... 436/82, 436/518; 435/7.1, 7.2
See application file for complete search history.

(56) References Cited

U.S. PATENT DOCUMENTS

| 5,091,404 | A | 2/1992 | Elgebaly |
| 5,270,163 | A | 12/1993 | Gold et al. |
| 5,403,914 | A | 4/1995 | Elgebaly |
| 5,504,013 | A | 4/1996 | Senior |
| 5,606,027 | A | 2/1997 | Elgebaly |
| 5,622,871 | A | 4/1997 | May et al. |
| 6,235,241 | B1 | 5/2001 | Catt et al. |
| 6,399,398 | B1 | 6/2002 | Cunningham et al. |
| 6,670,138 | B2 | 12/2003 | Gonzalez-Zulueta et al. |
| 2005/0137481 | A1 | 6/2005 | Sheard et al. |

FOREIGN PATENT DOCUMENTS

| WO | WO 91/19813 | 12/1991 |
| WO | WO 92/05285 | 4/1992 |
| WO | WO 92/14843 | 9/1992 |
| WO | WO 03/074069 | 9/2003 |

OTHER PUBLICATIONS

Trueba et al. (J Bacteriology 1992 vol. 174, p. 4761-4768.*
Trueba et al. Characterization of the periplasmic flagellum proteins of Leptospira interrogans. J. Bacteriol. 174 (14): 4761.1992.*
Elgebaly et al. Partial purification of a novel cardiac-derived neutrophil checotactic factor: Nourin-1. Circulation. 1993, 88:1-240 (Abstract).*
Burgess, et al. Possible dissociation of the heparin-binding and mitogenic activities of heparin-binding growth factor-1 from its receptor-binding activities by site-directed mutagenesis of a single lysine residue. J Cell Biol. 111:2129-2138, 1990.*
Alpert, J.S., et al. "Myocardial Infarction Redefined—A Consensus Document of The Joint European Society of Cardiology/American College of Cardiology Committee for the Redifinition of Myocardial Infarction" *J. Am. Coll. Cardiol.* 2000; 36; 959-69.
Boersma, E., et al. "Platelet glycoprotein IIb/IIIa inhibitors in acute coronary syndromes: a meta-analysis of all major randomised clinical trials" *Lancet* 2002: 359: 189-98.
Brennan, M.L., et al. "Prognostic Value of Myeloperoxidases in Patients with Chest Pain" *N. Engl. J. Med.* 2003; 349:1595-604.

Christenson, R.H., et al. "Characteristics of an Albumin Cobalt Binding Test for Assessment of Acute Coronary Syndrome Patients: A Multicenter Study" *Clin. Chem.* 2001; 47:464-470.
Christenson, R.H. and Azzazy, H.M.E., "Biochemical markers of acute coronary syndromes" *Clin. Chem.* 44, 1855-64, 1998.
Danne, O., et al. "Prognostic Implications of Elevated Whole Blood Choline Levels in Acute Coronary Syndrome" *Am. J. Cardiol.* 2003; 91: 1060-7.
de Lemos, J.A., et. al. "The Prognostic Value of Serum Myoglobin in Patients With Non-ST-Segment Elevation Acute Coronary Syndromes" *J. Am. Coll. Cardiol.* 2002; 40:238-44.
Doherty, D.E. et al. "Human Monocyte Adherence: A Primary Effect of Chemotactic Factors on the Monocyte to Stimulate Adherence to Human Endothelium" *J. Immunol.* 138(6), 1762-1771, 1987.
Elgebaly, S.A., et al. "Cardiac Derived Neutrophil Chemotactic Factors; Preliminary Biochemical Characterization" *J. Mol. Cell Cardiol.*, 21:585-593, 1989.
Elgebaly, S.A., et al. "Cyclocreatine Inhibits the Production of Neutrophil Chemotactic Factors from Isolated Hearts" *Am J. Pathol.* 137: 1233-1241, 1990.
Elgebaly, *J. Thorac. Cardiovasc. Surg,* "Cardiac-derived neutrophil chemotactic factors: Detection in coronary sinus effluents of patients undergoing myocardial revascularization" 130(5): 952-959, 1992.
Elgebaly, S.A., et al. "Evidence of Cardiac Inflammation After Open Heart Operations" *Ann. Thorac. Surg.* 57:391-396, 1994.
Joyce, "Amplification, mutation and selection of catalytic RNA" (1980), *Gene* 82:83-87.
Kleinfeld, A.M., et al. "Increases in Serum Unbound Free Fatty Acid Levels Following Coronary Angioplasty" *Am. J. Cardiol.* 1996: 78:1350-4.
Lucchesi, B.R., et al. "Leukocytes and Ischemia-induced Myocardial Injury" *Annu Rev. Pharmacol. Toxicol.* 26, 201-224, 1986.
Newby, L.K., et al. "Bedside Multimarker Testing for Risk Stratification in Chest Pain Units" *Circulation* 2001: 103; 1832-7.
Szostak et al. "In vitro selection of RNA molecules that bind specific ligands" (1990) *Nature* 346: 818-822.
Tuerk et al. "Systematic Evolution of Ligands by Exponential Enrichment: RNA Ligands to Bacteriophage T4 DNA Polymerase" (1990), *Science* 249: 505-510.
Yamamoto, Yuri et al., "Inhibitory Effects of Spinorphin, a Novel Endogenous Regulator, on Chemotaxis, $O_2$ Generation, and Exocytosis by N-Formylmethionyl-leucyl-phenylalanine (FMLP)-Stimulated Neutrophils" *Biochemical Pharmacology*, 54; 695-701, 1997.
Beattie M.S., Trends in Molecular Medicine, 2004, vol. 19, No. 12, pp. 580-583.
Yamazaki et al., European Journal of Pharmacology, 2001, vol. 413, pp. 173-178.
O'Flaherty et al., The Journal of Immunology, 1978, vol. 120, No. 4, pp. 1326-1332.
Le et al., Trends in Immunology, 2002, vol. 23, No. 11, pp. 541-548.
Lutsenko et al., Proc. Natl. Acad. Sci., 1998, vol. 95, pp. 6004-6009.
Koehler et al., Proc. Natl. Acad. Sci., 1999, vol. 96, pp. 2141-2146.

* cited by examiner

*Primary Examiner*—Maher M Haddad
(74) *Attorney, Agent, or Firm*—Latimer & Mayberry IP Law LLP

(57) ABSTRACT

An inflammatory peptide can be a marker for cardiac ischemia.

14 Claims, 2 Drawing Sheets

Plasma from Normal Controls and ACS Patients

Plasma from Normal Controls and ACS Patients

DIAGNOSTIC MARKER

TECHNICAL FIELD

This invention relates to a marker of cardiovascular disease and cardiovascular events.

BACKGROUND

Atherosclerosis is an inflammatory process in which deposits of fatty substances, cholesterol, cellular waste products, calcium and other substances form plaque in the inner lining of an artery. Plaques can grow large enough to significantly reduce the flow of blood through an artery, such as a coronary artery. If a plaque ruptures, a clot can form at the site of the plaque. The clot can block the artery partially or completely. When tissue is deprived of sufficient oxygen (for example, because of reduced blood flow in a narrowed or blocked artery), the tissue becomes ischemic. If the ischemia is severe or persistent, cell death (necrosis) can occur. When a coronary artery is blocked, a heart attack (myocardial infarction) can result. Inflammation can contribute to all stages of cardiovascular disease from plaque formation and acute rupture leading to occlusion, ischemia, and infarction.

Cardiac markers serve an important role in the early detection and monitoring of cardiovascular disease. Markers of disease are typically substances found in a bodily sample that can be easily measured. The measured amount can correlate to underlying disease pathophysiology, presence or absence of a current or imminent cardiac event, probability of a cardiac event in the future. In patients receiving treatment for their condition the measured amount will also correlate with responsiveness to therapy. Markers can include elevated levels of blood pressure, cholesterol, blood sugar, homocysteine and C-reactive protein (CRP). However, current markers, even in combination with other measurements or risk factors, do not adequately identify patients at risk, accurately detect events (i.e., heart attacks), or correlate with therapy. For example, half of patients do not have elevated serum cholesterol or other traditional risk factors.

Myocardial ischemia is the main cause of the acute coronary syndromes (ACS), a continuum of disease that spans from unstable angina (characterized by reversible cardiac ischemia) to myocardial infarction with large areas of necrosis. Myocardial ischemia can result from thrombus formation after plaque rupture in a coronary artery. The acute coronary syndromes represent a complex and heterogeneous physiological condition. Although remarkable therapeutic and technological advances over the past 20 years have reduced the in-hospital mortality of acute myocardial infarction, this progress has been limited to patients who display ST-elevation on their electrocardiogram (ECG). ST-elevation is an indicator of myocardial infarction, and treatment within 12 hours of symptoms onset will improve the outcome. However, only about 50% of myocardial infarction patients have diagnostic ECG changes. The remaining patients must be observed for clinical monitoring signs and biochemical markers such as cardiac troponin T or I.

Cardiac troponin has become the cornerstone for diagnosis of myocardial infarction. Markers such as CK-MB and myoglobin can be useful for assessment and risk stratification of suspected ACS patients. Compelling evidence indicates that an elevated cardiac troponin can identify high-risk ACS patients that benefit from treatment with inhibitors of the glycoprotein IIb/IIIa platelet receptor. However, troponin, CK-MB and myoglobin are markers of necrosis and therefore offer no information regarding myocardial ischemia that occurred before cell death. A test that can accurately detect the presence or absence of myocardial ischemia allowing treatment decisions to be made at an earlier stage of the ACS continuum will have significant clinical utility. Further, therapeutic options specifically targeting this early stage of ACS has the potential to significantly improve patient prognosis.

SUMMARY

A cardiac marker of ischemia can be used to identify patients who should receive appropriate therapy or intervention while cell damage is reversible (such as before ischemia progresses to necrosis, or when there is an increased risk of ischemia). Such a marker can help to detect myocardial ischemia or assess or predict risk of myocardial ischemia, particularly before cell death occurs. Early detection of ischemia or prediction of the risk of ischemia can allow early treatment and thereby improve patient outcome. When the marker is also an early inflammatory signal, a patient can benefit from treatment that blocks or interferes with that signal.

For optimum diagnostic usefulness, a cardiac marker in the bloodstream should be present in a high concentration in the myocardium and absent from non-myocardial tissue. The marker should be rapidly released into the blood after myocardial ischemia with a direct proportional relationship between the extent of myocardial ischemia and the measured level of the marker. Finally, the marker should persist in blood for a sufficient length of time to provide a convenient diagnostic time window with an easy, inexpensive, and rapid assay technique.

Current cardiac markers, such as CK-MB and Troponin I, are released 4 to 8 hours after the onset of chest pain, and are released after irreversible injury (i.e., necrosis) has occurred. Nourin-1 is an inflammatory polypeptide released within 5 minutes by heart tissues in response to myocardial ischemia. Nourin-1 can be detected within minutes in blood samples obtained from patients experiencing ACS, indicating that reversible and irreversible ischemic injury has occurred, dependent on whether markers of cardiac injury are also elevated.

In one aspect, a method of monitoring cardiac health includes obtaining a sample from a patient and detecting a level of Nourin-1 in the sample. Detecting a level of Nourin-1 can include contacting the sample with an antibody that recognizes Nourin-1. The sample can be taken from the patient before, during, or after a stress test. The method can include assessing the patient for the presence of a cardiac risk factor. The cardiac risk factor can be smoking, an adverse lipid profile, an elevated level of lipid, an elevated level cholesterol, diabetes, hypertension, a hypercoagulable state, or an elevated level of homocysteine. In certain circumstances, the patient has been treated for a cardiac condition. The method can include treating the patient for a cardiac condition, and detecting a level in a second sample to monitor treatment.

In another aspect, a method of detecting cardiac ischemia in a patient includes obtaining a sample from a patient suspected of suffering cardiac ischemia or other cardiac event, and contacting the sample with an antibody that recognizes Nourin-1 to detect a level of Nourin-1.

The sample can include blood, blood plasma, serum, interstitial fluid, saliva, cardiac tissue, or urine. The sample can be taken from a patient suspected of suffering cardiac ischemia or other cardiac event.

In another aspect, a synthetic polypeptide includes a first sequence selected from the group consisting of:

-QKPSPSTMR- (SEQ ID NO: 1),
-HALYDEMR- (SEQ ID NO: 2),
-MIINHNLAAINSHR- (RESIDUES 1-14 OF SEQ ID NOS 15-17),
-AQRIGVPSR- (SEQ ID NO: 3),
-MNTRAMNDASGR- (SEQ ID NO: 4),
-LAAQGLDALPR- (SEQ ID NO: 5),
-MENHK- (SEQ ID NO: 6),
-VGAFKN- (SEQ ID NO: 7),
-SPGADGNGGEAMPGGG- (RESIDUES 15-30 OF SEQ ID NOS 15-17),
-GTVGPDVIDIR- (SEQ ID NO: 8),
-KSQNMALMGGLTK- (SEQ ID NO: 9),
-ELLHYCLLREIPFFYA- (SEQ ID NO: 10),
-YAVLCGGGANHRLGLT- (SEQ ID NO: 11),
-MIGTGGFIGASLR- (SEQ ID NO: 12),
-VGDYVVHVNHGIGK- (SEQ ID NO: 13), and
-VVVGTLDPNPLVSGK- (SEQ ID NO: 14).

In another aspect, a synthetic polypeptide includes the sequence -MIINHNLAAINSHRSPGADGNGGEAMPGGG- (SEQ ID NO: 15).

The first sequence can include a substitution. The substitution can be a conservative substitution. The polypeptide can include a second sequence selected from the group consisting of:
-QKPSPSTMR- (SEQ ID NO: 1),
-HALYDEMR- (SEQ ID NO: 2),
-MIINHNLAAINSHR- (RESIDUES 1-14 OF SEQ ID NOS 15-17),
-AQRIGVPSR- (SEQ ID NO: 3),
-MNTRAMNDASGR- (SEQ ID NO: 4),
-LAAQGLDALPR- (SEQ ID NO: 5),
-MENHK- (SEQ ID NO: 6),
-VGAFKN- (SEQ ID NO: 7),
-SPGADGNGGEAMPGGG- (RESIDUES 15-30 OF SEQ ID NOS 15-17),
-GTVGPDVIDIR- (SEQ ID NO: 8),
-KSQNMALMGGLTK- (SEQ ID NO: 9),
-ELLHYCLLREIPFFYA- (SEQ ID NO: 10),
-YAVLCGGGANHRLGLT- (SEQ ID NO: 11),
-MIGTGGFIGASLR- (SEQ ID NO: 12),
-VGDYVVHVNHGIGK- (SEQ ID NO: 13), and
-VVVGTLDPNPLVSGK- (SEQ ID NO: 14), where the second sequence differs from the first sequence.

The second sequence can include a substitution. The substitution can be a conservative substitution. The polypeptide can include the sequence: -MIINHNLAAINSHR- (RESIDUES 1-14 OF SEQ ID NOS 15-17), or -SPGADGNGGEAMPGGG- (RESIDUES 15-30 OF SEQ ID NOS 15-17). The polypeptide can include the sequence -MIINHNLAAINSHRSPGADGNGGEAMPGGG- (SEQ ID NO: 15). The polypeptide can include the sequence -MIINHNLAAINSHRSPGADGNGGEAMPGGGK- (SEQ ID NO: 16). The polypeptide can include the sequence -MIINHNLAAINSHRSPGADGNGGEAMPGGGR- (SEQ ID NO: 17). The polypeptide can include the sequence N-formyl-MIINHNLAAINSHR- (RESIDUES 1-14 OF SEQ ID NOS 15-17). The polypeptide can include the sequence N-formyl-MIINHNLAAINSHRSPGADGNGGEAMPGGG- (SEQ ID NO: 15). The polypeptide can have a molecular weight of no greater than 10 kDa. The polypeptide can have a neutrophil chemotactic activity.

In another aspect, an antibody derived from a mammal immunized with a synthetic polypeptide, the polypeptide including a first sequence selected from the group consisting of:
-QKPSPSTMR- (SEQ ID NO: 1),
-HALYDEMR- (SEQ ID NO: 2),
-MIINHNLAAINSHR- (RESIDUES 1-14 OF SEQ ID NOS 15-17),
-AQRIGVPSR- (SEQ ID NO: 3),
-MNTRAMNDASGR- (SEQ ID NO: 4),
-LAAQGLDALPR- (SEQ ID NO: 5),
-MENHK- (SEQ ID NO: 6),
-VGAFKN- (SEQ ID NO: 7),
-SPGADGNGGEAMPGGG- (RESIDUES 15-30 OF SEQ ID NOS 15-17),
-GTVGPDVIDIR- (SEQ ID NO: 8),
-KSQNMALMGGLTK- (SEQ ID NO: 9),
-ELLHYCLLREIPFFYA- (SEQ ID NO: 10),
-YAVLCGGGANHRLGLT- (SEQ ID NO: 11),
-MIGTGGFIGASLR- (SEQ ID NO: 12),
-VGDYVVHVNHGIGK- (SEQ ID NO: 13), and
-VVVGTLDPNPLVSGK (SEQ ID NO: 14)

The antibody can be a polyclonal antibody or a monoclonal. The antibody can recognize Nourin-1. The antibody can inhibit a biological activity of Nourin-1. The antibody can be immobilized on a substrate. The antibody can be derived from a mammal immunized with Nourin-1.

In another aspect, a method of detecting a level of Nourin-1 in a sample having contacted cardiac muscle includes contacting the sample with an antibody that recognizes Nourin-1.

In another aspect, a method of detecting a level of Nourin-1 in a sample includes contacting the sample with an antibody derived from a mammal immunized with a synthetic polypeptide having a neutrophil chemotactic activity.

In another aspect, a method of detecting Nourin-1 in a sample includes contacting the sample with an antibody derived from a mammal immunized with a synthetic polypeptide comprising a first sequence selected from the group consisting of:
-QKPSPSTMR- (SEQ ID NO: 1),
-HALYDEMR- (SEQ ID NO: 2),
-MIINHNLAAINSHR- (RESIDUES 1-14 OF SEQ ID NOS 15-17),
-AQRIGVPSR- (SEQ ID NO: 3),
-MNTRAMNDASGR- (SEQ ID NO: 4),
-LAAQGLDALPR- (SEQ ID NO: 5),
-MENHK- (SEQ ID NO: 6),
-VGAFKN- (SEQ ID NO: 7),
-SPGADGNGGEAMPGGG- (RESIDUES 15-30 OF SEQ ID NOS 15-17),
-GTVGPDVIDIR- (SEQ ID NO: 8),
-KSQNMALMGGLTK- (SEQ ID NO: 9),
-ELLHYCLLREIPFFYA- (SEQ ID NO: 10),
-YAVLCGGGANHRLGLT- (SEQ ID NO: 11),
-MIGTGGFIGASLR- (SEQ ID NO: 12),
-VGDYVVHVNHGIGK- (SEQ ID NO: 13), and
-VVVGTLDPNPLVSGK- (SEQ ID NO: 14).

In another aspect, a method of preventing, inhibiting, or treating inflammation in a patient includes administering a Nourin-1 antagonist.

The inflammation can be inflammation of cardiac tissue. The Nourin-1 antagonist can include an antibody that recognizes Nourin-1. The antibody can be derived from a mammal immunized with Nourin-1.

The method can include detecting a level of a first marker associated with cardiac ischemia, cardiac necrosis, inflammation, plaque rupture, thrombus formation, platelet aggregation or activation, myocardial conduction, or myocardial infarction, wherein the first marker is other than Nourin-1, in a sample taken from the patient.

The first marker can be creatine kinase, creatine kinase-MB, troponin I, troponin T, myoglobin, fibrinopeptide, fibrinogen, C reactive protein, serum amyloid A, interleukin-6, intercellular adhesion molecule-1, vascular cell adhesion molecule-1, E-selectin, soluble P-Selectin, soluble CD40 ligand, activated platelets, monocyte-platelet aggregates, oxidized-LDL, MDA-modified LDL, ischemia-modified albumin, free fatty acid, oxygen-regulated peptide 150, or electrocardiogram.

The method can include detecting a level of a second marker associated with cardiac ischemia, cardiac necrosis, inflammation, or myocardial infarction, wherein the second marker is other than Nourin-1, in a sample taken from the patient.

The first marker can be creatine kinase, creatine kinase-MB, troponin I, troponin T, or myoglobin, and the second marker can be different from the first marker while being creatine kinase, creatine kinase-MB, troponin I, troponin T, or myoglobin.

The patient can be a mammal. The patient can be a human.

The details of one or more embodiments are set forth in the accompanying drawings and the description below. Other features, objects, and advantages will be apparent from the description and drawings, and from the claims.

DETAILED DESCRIPTION

Figure 1:
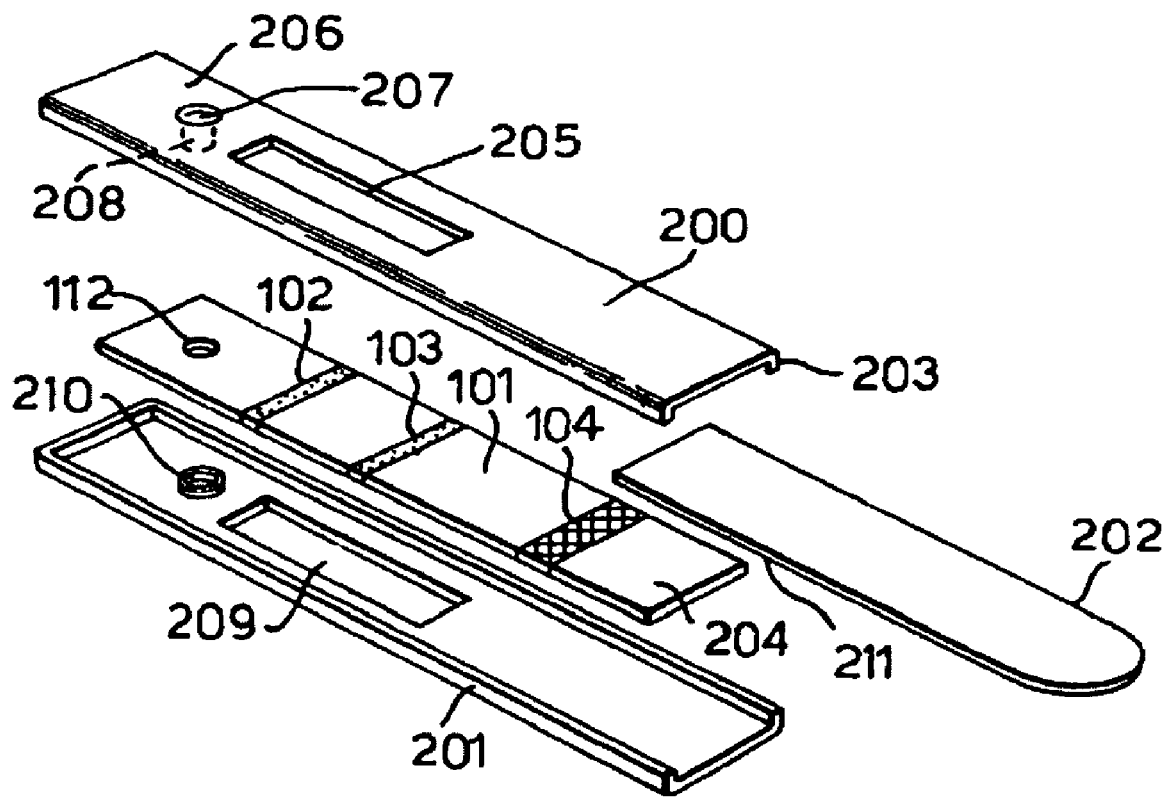
FIG. 1 is a schematic view of a diagnostic device.

Coronary artery disease is the leading cause of death in the United States. A frequent manifestation of coronary artery disease is acute coronary syndrome, a constellation of clinical symptoms compatible with acute myocardial ischemia. If a patient arrives in the emergency room with an acute myocardial infarction (AMI) characterized by elevation of the ST segment of the ECG, prompt treatment is indicated, for example, with balloon angioplasty. On the other hand, if a patient's symptoms do not include ST-elevation, the diagnosis is more ambiguous. The patient may have unstable angina or a non-ST-segment elevation myocardial infarction (NSTEMI). These are two closely related conditions, having similar clinical presentations and pathogenesis. However, they differ in severity and may be distinguished by the release of detectable amounts of markers of myocardial injury. Frequently used markers include troponin I, troponin T, and the MB isoenzyme of creatine kinase (CK-MB). See, for example, Christenson, R. H., and Azzazy, H. M. E. *Clin. Chem.* 44, 1855-64, 1998; and Braunwald, E., et al. ACC/AHA 2002 Guideline Update for the Management of Patients With Unstable Angina and Non-ST-Segment Elevation Myocardial Infarction, 2002, available at http://www.acc.org/clinical/guidelines/unstable.pdf, each of which is incorporated by reference in its entirety. Because there is a delay between myocardial injury and the increase in serum levels of these markers, it is not always possible to distinguish patients suffering unstable angina from those suffering a NSTEMI when the patient is first evaluated.

The patient with heart attack-like symptoms may turn out to be suffering from a different cardiovascular condition (e.g., acute pericarditis), a non-cardiac condition associated with a disease (such as chest pain secondary to esophageal spasm), or an undefined, noncardiovascular condition.

Use of markers in diagnosis of cardiac conditions is described in, for example, Alpert, J. S., et al. *J. Am. Coll. Cardiol.* 2000; 36:959-69; Newby, L. K., et al. *Circulation* 2001:103; 1832-7; de Lemos, J. A., et al. *J. Am. Coll. Cardiol.* 2002; 40:238-44; Boersma, E., et al. *Lancet* 2002; 359:189-98; Christenson, R. H., et al., *Clin. Chem.* 2001; 47:464-470; Kleinfeld, A. M., et al. *Am. J. Cardiol.* 1996; 78:1350-4; Brennan, M. L., et al. *N. Engl. J. Med.* 2003; 349:1595-604; and Danne, O., et al. *Am. J. Cardiol.* 2003; 91:1060-7, each of which is incorporated by reference in its entirety.

Chemical signals which participate in the recruitment and activation of neutrophils (i.e. neutrophil chemotactic factors) into ischemic myocardium are of great interest as potential markers of cardiac ischemia. Neutrophil chemotactic factors are inflammatory mediators which recruit neutrophils from circulation to sites of tissue damage, increase adhesion of cells to these sites, and activate neutrophils to release toxic agents such as oxygen metabolites and proteases (see, for example, Doherty, D. E., et al. *J. Immunol.* 138 (6), 1762-1771, 1987, which is incorporated by reference in its entirety). Neutrophils accumulate in the myocardium during reperfusion in animal models of coronary artery occlusion and cardioplegic cardiac arrest. Neutrophil accumulation after ischemia is associated with myocardial cell injury, ventricular arrhythmias, and capillary no-reflow phenomena (see, for example, Lucchesi, B. R., et al. *Annu. Rev. Pharmacol. Toxicol.* 26, 201-224, 1986, which is incorporated by reference in its entirety).

The neutrophil chemotactic factor Nourin-1 is rapidly released by ischemic and infarcted myocardium. Nourin-1 is a small (~3 kDa), heat labile protein, with an isoelectric point between pH 7.0 and pH 8.0. Like many small inflammatory mediators in circulation, Nourin-1 can be found associated with a larger carrier having a molecular weight between 100 and 300 kDa in size. The association between the larger carrier and Nourin-1 is non-covalent. Nourin-1 can be purified from cardioplegic effluents collected during cardiac arrest from patients undergoing coronary bypass surgery. Other chemotactic factors such as the complement component C5a, interleukin-8, interleukin-1, and leukotriene B4 were not detected in patients' cardioplegic effluents from which Nourin-1 was purified. See, for example, Elgebaly, S. A., et al. *J. Mol. Cell. Cardiol.* 21:585-593, 1989; Elgebaly, S. A., et al. *Am. J. Pathol.* 137:1233-1241, 1990; Elgebaly, S. A., et al., *J. Thorac. Cardiovasc. Surg.* 103(5):952-959, 1992; Elgebaly, S. A., et al., *Circulation* 86(4), 1992; Elgebaly, S. A., et al., *Circulation* 88(4), 1993; Tyles, E., et al. *Circulation* 90(4), 1994; Elgebaly, S. A., et al. *Ann. Thorac. Surg.* 57:35-41, 1994; and Tyles, E., et al. *Circulation* 92(8), 1995, each of which is incorporated by reference in its entirety.

Nourin-1 is one of the initial signals for the inflammatory response and serves several fundamental roles for mounting an effective response to the physiological stresses resulting from myocardial ischemia. Nourin-1 is released in response to both reversible and irreversible tissue ischemia. It functions as a potent inflammatory signal and mediator in the development of post-ischemic cardiac inflammation and recruitment of cells such as neutrophils and mononuclear cells to the site of ischemia. Nourin-1 stimulates neutrophils and mononuclear cells. More specifically, Nourin-1 stimulates the secretion of interleukin-8 (IL-8) by neutrophils and mononuclear cells; the secretion of interleukin-1 (IL-1) and tumor necrosis factor by mononuclear cells; and the release of high levels of collagenase by neutrophils and mononuclear cells to facilitate migration of these cells into tissue. Nourin-1 also induces the expression of adhesion molecules by neutrophils (LECAM) and endothelial cells (ICAM-1 and ELAM-1). These adhesion molecules facilitate the migration of neutrophils and mononuclear cells to the site of tissue damage. Nourin-1 mediated induction of the pro-inflammatory mediators cytokines IL-1 and IL-8 will likely induce synthesis of C-reactive protein (CRP) by the liver, and appears to be the very earliest signal for inducing the inflammatory response and synthesis of this potent risk factor. Monoclonal antibodies to Nourin-1 blocked the chemotactic effect of Nourin-1. The antibodies were also able to inhibit IL-8 release. See, for example, U.S. Pat. Nos. 5,403,914 and 5,606,027, each of which is incorporated by reference in its entirety. Because it is a functional chemotactic factor that is an essential part of the early inflammatory response, Nourin-1 is a promising marker for myocardial ischemia.

Determining whether a patient has a higher than normal amount of Nourin-1 in his or her bloodstream can help distinguish a patient suffering a heart condition (for example, unstable angina, a non-ST elevation myocardial infarction, or AMI) from a patient suffering from a condition that does not involve the heart. Nourin-1 can also be a risk marker, where elevated levels in individuals with known or unknown ischemic heart disease can provide a measure of risk for future events. The treatment regimen for a patient can be chosen based on the results of a Nourin-1 test, either alone or in combination with other factors. The other factors can include results of other tests, such as an ECG, tests for levels of other cardiac markers such as myoglobin, creatine kinase, CK-MB, troponin I, or troponin T; or tests for other proteins associated with heart disease, including fibrinopeptide, fibrinogen, C reactive protein, serum amyloid A, interleukin-6, intercellular adhesion molecule-1, vascular cell adhesion molecule-1, and E-selectin. Other markers include soluble P-selectin, soluble CD40 ligand, activated platelets, monocyte-platelet aggregates, oxidized-LDL, MDA-modified LDL, ischemia-modified albumin, free fatty acid, and oxygen-regulated peptide 150. A patient can be tested for Nourin-1 and one or more additional markers indicative of risk or an ACS event. Advantageously, because Nourin-1 is released quickly after the onset of myocardial ischemia, treatment decisions can be made while the myocardial ischemia is reversible.

Nourin-1 can be a biomarker for cardiac ischemia or cardiac injury arising from ischemia or other causes. For example, an elevated level of Nourin-1 can be associated with cardiac injury from cardiovascular disease, ischemia, as a side effect of a drug treatment, or surgery.

The level of Nourin-1 can be used to assess or predict risk of ischemia. For example, a patient's risk of heart attack or other cardiac event can be influenced by the level of Nourin-1 and the presence, absence or degree of a risk factor. The risk factor can include, for example, smoking, adverse lipid profiles, elevated lipids or cholesterol, diabetes, hypertension, hypercoagulable states, elevated homocysteine levels, genetic factors, other biochemical markers, family history, or lack of exercise. Detection of a level of Nourin-1 in combination with one or more risk factor can assess or predict risk of ischemia. For example, if Nourin-1 is detected in a patient that has an elevated cholesterol level, the patient can be at higher risk of cardiac ischemia than a patient with an average cholesterol level.

Inflammation is a major contributor to cardiovascular disease playing a major role in all stages from plaque formation and acute rupture leading to occlusion, ischemia, and infarction. Current inflammation markers, such as CRP, can be non-specific. In other words, the current inflammation markers can be present for reasons other than cardiac inflammation. Because it is a component of the inflammatory response in cardiac tissue, Nourin-1 can be a useful marker of inflammation. Determining a patient's Nourin-1 level, and identifying the presence or absence of another biochemical marker, such as CRP, can be useful in understanding that patient's risk of a future cardiac event.

Because Nourin-1 can be a marker of cardiac ischemia, it can be useful to test a patient's Nourin-1 level before, during or after a stress test, to determine if the stress test induces cardiac ischemia. A stress test can use exercise or drugs to stress the patient's cardiovascular system. Typically, a patient's response to a stress test is measured by ECG; however, it can be difficult to measure ischemia in these patients. In particular, an ECG can be difficult to interpret for a patient who has had a previous heart attack. A stress test can also be performed in conjunction with imaging of the heart, for example, using a radioactive agent and camera that detects the radioactivity to provide images of the heart. The images can reveal the location and extent of ischemia induced by stress. Detecting a level of Nourin-1 during a stress test can allow the test to provide a more accurate assessment of the risk of cardiac ischemia in the patient.

The progress of therapy in a patient can be monitored by detecting a level of Nourin-1 in the patient. For example, a patient who is taking statin drugs, which can have an anti-inflammatory effect, can have his or her Nourin-1 level determined, for example, at different time points during therapy. Changes in Nourin-1 level can correlate with the progress of therapeutic treatments. In some circumstances, combinations of Nourin-1 levels with levels of other risk factors, such as lipids, can be effective in determining the progress of therapy.

A test can determine the presence of Nourin-1 in a biological sample. The sample can be a body fluid, e.g., blood or urine, or the sample can be a material that has contacted cardiac tissue, such as blood or a cardioplegic effluent. The test can be qualitative or quantitative. The test can be in an immunochromatographic format. A qualitative test can be distinguish between the presence or absence of Nourin-1, or can distinguish between categories of Nourin-1 levels in a sample, such as absent, low concentration, medium concentration or high concentration. A quantitative test can provide a numerical measure of Nourin-1 in a sample. The test can include contacting Nourin-1 with an antibody that recognizes Nourin-1. The test can include detecting Nourin-1 by mass spectrometry. The test can include a test for Nourin-1 function (for example, a test for chemotactic effect). The test can include assaying a sample including cells for expression (e.g., of mRNA or polypeptide) of the Nourin-1 gene by the cells. The test can include a combination of measurements, for example, the test can include contacting a sample with an antibody that recognizes Nourin-1 and a mass spectrometry measurement.

Antibodies to Nourin-1 can be used to detect the presence of Nourin-1. For example, in a sandwich assay, antibodies to Nourin-1 can be immobilized on a surface. A sample of interest is allowed to interact with the immobilized antibodies. If Nourin-1 is present in the sample, it will be bound by the antibodies and thus become immobilized. After incubation, the surface can be washed prior to addition of a second antibody to Nourin-1. The second antibody can recognize a different epitope of nourin than the immobilized antibody. If Nourin-1 was present in the initial sample, an immobilized antibody/Nourin-1/second antibody sandwich forms. The second antibody can be coupled to a colored material, or alternatively, the sandwich can then be detected by a third antibody. Typically the third antibody is an anti-IgG antibody derived from a different species than the second antibody. For example, if the second antibody to Nourin-1 is a mouse IgG, then the third antibody can be a goat anti-mouse IgG antibody or a rabbit anti-mouse IgG antibody.

The second or third antibody can produce a detectable change when bound to its target. For ease of detection of the sandwich, the second or third antibody can be associated with a color-developing reagent. The color-developing reagent can be a colored material (such as a dye or colored latex particle) or a reagent capable of converting a colorless material to a colored material. One such reagent is a peroxidase enzyme linked to the third antibody. In the presence of appropriate substrates, the peroxidase enzyme can produce a colored product, which is easily detected by virtue of its color. The use of an enzyme (or other catalyst) to produce a detectable change in samples having Nourin-1 can increase the sensitivity of the assay. Other methods of detecting an antigen (such as Nourin-1) using antibodies to the antigen are known.

Another method of detecting Nourin-1 includes the use of a ligand. A ligand can include, for example, a modified antibody, chimeric antibody, soluble receptor, aptamer, or other species capable of binding to Nourin-1. The higher-molecular weight carrier associated with Nourin-1 can be a ligand to Nourin-1. An aptamer is a single- or double-stranded DNA or single-stranded RNA molecules that recognize and bind to a desired target molecule by virtue of their shapes. See, e.g., PCT Publication Nos. WO 92/14843, WO 91/19813, and WO 92/05285, each of which is incorporated by reference in its entirety. The ligand can be detectably labeled, for example with a fluorescent dye, colored material, or radioactive isotope.

Examples of immunochromatographic tests and test result readers can be found in, for example, U.S. Pat. Nos. 5,504,013; 5,622,871; 6,235,241; and 6,399,398, each of which is incorporated by reference in its entirety.

Referring to FIG. 1, an assay device can include a plastic casing having upper and lower halves 200 and 201 adapted to contain assay strip 101 and also a bibulous sample receiving member 202 which can extend out of one end 203 of the assembled casing. In the assembled device the bibulous receiving member 202 overlaps the end 204 of the assay strip adjacent to a mobile labeled reagent 104. Mobile labeled reagent 104 can be, for example, an antigen (e.g., a labeled Nourin-1) or an antibody (e.g., a labeled antibody that recognizes Nourin-1). The label can be, for example, a particulate direct label such as colored latex. The upper half 200 of the casing includes a window or aperture 205 through which first detection zones 102 and optional second detection zone 103 can be observed from outside the casing. Detection zones 102 and 103 can include, for example, a first immobilized antibody in detection zone 102, and a second different immobilized antibody in detection zone 103. The first immobilized antibody can bind the analyte of interest (e.g. Nourin-1) and the second immobilized antibody can bind a second analyte and act as a control. The upper half of the casing 200 contains on its external surface 206 a circular depression 207 on the central longitudinal access of the casing a short distance beyond the observation window relative to the end 203 of the casing accommodating the sample receiving member. On the inside of the upper half of the casing is a downwardly extending pin or peg 208 located directly below depression 207. The diameter of the downwardly extending pin or peg 208 matches that of the hole 112 in the assay strip 101, so that the strip can be positively located within the assembled device on the peg.

The lower half 201 of the casing optionally includes a light-transmitting window or aperture 209 which, in the assembled device, lies directly opposite to the result window 205 in the upper half of the casing. Lower half of the casing also contains a depression 210 which can accommodate the bottom end of the pin or peg 208 when the two halves of the casing are placed together to make an enclosure.

In the assembled device, the act of enclosing the strip and bibulous member between the upper and lower halves of the casing causes the overlapping portions 204 and 211 of the strip and bibulous member to be crimped together to provide a good moisture-conductive junction.

The biological sample that is tested for the presence of Nourin-1 can be any sample in which evidence of inflammation is suspected to be found. For example, if released from an ischemic heart, Nourin-1 can be detected in blood, blood plasma, serum, interstitial fluid, saliva, cardiac tissue, or urine, as well as tissue homogenates (e.g., using tissue collected in a biopsy) and cardioplegic effluents.

The structure of Nourin-1 can be described with a polypeptide sequence. For example, the structure can be described by a single polypeptide sequence representing the full polypeptide sequence of Nourin-1, or the structure can be described by a partial sequence, corresponding to a fragment of Nourin-1. A plurality of partial sequences can be combined to make a larger partial sequence or the full sequence. For example, a first polypeptide sequence can represent the N-terminal polypeptide sequence of Nourin-1, and a second sequence can represent the C-terminal polypeptide sequence of Nourin-1. A polypeptide sequence of Nourin-1 can include:
 -QKPSPSTMR- (SEQ ID NO: 1),
 -HALYDEMR- (SEQ ID NO: 2),
 -MIINHNLAAINSHR- (RESIDUES 1-14 OF SEQ ID NOS 15-17),
 -AQRIGVPSR- (SEQ ID NO: 3),
 -MNTRAMNDASGR- (SEQ ID NO: 4),
 -LAAQGLDALPR- (SEQ ID NO: 5),
 -MENHK- (SEQ ID NO: 6),
 -VGAFKN- (SEQ ID NO: 7),
 -SPGADGNGGEAMPGGG- (RESIDUES 15-30 OF SEQ ID NOS 15-17),
 -GTVGPDVIDIR- (SEQ ID NO: 8),
 -KSQNMALMGGLTK- (SEQ ID NO: 9),
 -ELLHYCLLREIPFFYA- (SEQ ID NO: 10),
 -YAVLCGGGANHRLGLT- (SEQ ID NO: 11),
 -MIGTGGFIGASLR- (SEQ ID NO: 12),
 -VGDYVVHVNHGIGK- (SEQ ID NO: 13), and
 -VVVGTLDPNPLVSGK- (SEQ ID NO: 14),
 -GSEV- (SEQ ID NO: 18),
 -VDQPD- (SEQ ID NO: 19),
 -VDKPD- (SEQ ID NO: 20),
 -GTVGPDVIDIR- (SEQ ID NO: 8),
 -WYLVDASGLVLGRLAV- (SEQ ID NO: 21), or
 -ADAFVYDAPYNVVAVD- (SEQ ID NO: 22).

Where polypeptide sequences are listed with a dash ("-") at one or both ends, the dash indicates a terminus, or an additional amino acid or peptide sequence occurring N-terminal or C-terminal to the sequence presented. The N- or C-terminus can be modified, such as with a formyl group on the N-terminus. The additional peptide sequence can be modified, (for example, glycosylated, phosphorylated, modified with a hydrophobic group (e.g., myristoylated or geranylgeranylated), or other peptide modification. If the polypeptide is synthetic, the modification can include, for example, a colored or fluorescent group, or a poly(ethylene glycol) group.

In general, an amino acid residue of the polypeptide can be replaced by another amino acid residue in a conservative substitution. Examples of conservative substitutions include, for example, the substitution of one non-polar (i.e., hydrophobic) residue such as isoleucine, valine, leucine or methionine for another non-polar residue; the substitution of one polar (i.e. hydrophilic) residue for another polar residue, such as a substitution between arginine and lysine, between glutamine and asparagine, or between glycine and serine; the substitution of one basic residue such as lysine, arginine or histidine for another basic residue; or the substitution of one acidic residue, such as aspartic acid or glutamic acid for another acidic residue. In an conservative substitution, an amino acid residue can be replaced with an amino acid residue having a chemically similar side chain. Families of amino acid residues having side chains with chemical similarity have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A conservative substitution may also include the use of a chemically derivatized residue in place of a non-derivatized residue. A chemical derivative a residue chemically derivatized by reaction of a functional group of the residue. Examples of such chemical derivatives include, but are not limited to, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters, or other types of esters or hydrazides. Free hydroxyl groups may be derivatized to form O-acyl or O-alkyl derivatives. Also included as chemical derivatives are those polypeptides which contain one or more naturally-occurring amino acid derivatives of the twenty standard amino acids. For example, 4-hydroxyproline may be substituted for proline; 5-hydroxylsine may be substituted for histidine; homoserine may be substituted for serine; and ornithine may be substituted for lysine.

An amino acid residue of the polypeptide can be replaced by another amino acid residue in a non-conservative substitution. In some cases, a non-conservative substitution will not alter the relevant properties of the polypeptide. The relevant properties can be, without limitation, chemotactic activity for neutrophils, ability to bind to an antibody that recognizes Nourin-1, or other biological activity.

In general, polyclonal antibodies that recognize a particular polypeptide can be generated by immunizing a mammal (such as a mouse or rabbit) with the polypeptide. The polypeptide can be Nourin-1, a fragment or cleavage product of Nourin-1, or a Nourin-1 analog. The polypeptide can include other sequences besides a Nourin-1 sequence. The Nourin-1 analog can be biologically active (i.e., sharing some or all of the biological effects of Nourin-1, such as promoting chemotaxis) or biologically inactive. Whether biologically active or inactive, the analog can serve as an antigen for generating antibodies that recognize Nourin-1. The polypeptide antigen can have a molecular weight of at least 20 kDa for development of a strong immune response in animals. If the polypeptide has a molecular weight less than 20 kDa, it can be linked to a larger polypeptide by chemical methods, or cloned and expressed as a fusion with a larger polypeptide. The polypeptide antigen can be injected as a mixture with an adjuvant, such as Freund's complete adjuvant. An ELISA assay can be used to determine the titer of antibodies in serum collected from the animal. Detailed procedures for the generation of polyclonal antibodies can be found, for example, in *Current Protocols in Immunology*, 2001, John E. Coligan, ed., John Wiley & Sons.

In general, monoclonal antibodies that recognize a particular polypeptide can be generated by immunizing a BALB/c mouse with the polypeptide. If the polypeptide has a molecular weight less than 20 kDa, it can be linked to a larger polypeptide by chemical methods, or cloned and expressed as a fusion with a larger polypeptide. The polypeptide antigen can be injected as a mixture with an adjuvant, such as Freund's complete adjuvant. Spleen cells from the immunized mouse can be fused with myeloma cells to form immortal, antibody-expressing cells. Cells that express an antibody having specificity for the desired polypeptide can be isolated and used to produce additional quantities of the monoclonal antibody. Detailed procedures for the generation of polyclonal antibodies can be found, for example, in *Current Protocols in Immunology*, 2001, John E. Coligan, ed., John Wiley & Sons.

When an antibody is made by the methods described above, it can be described as being derived from a mammal (i.e., a mouse or rabbit in the description above). A monoclonal antibody produced from a hybridoma cell culture is considered to be derived from the mammal, since the hybridoma is made by fusing cells from the mammal immunized with an antigen.

Methods for generating a target-specific aptamer are described in, for example, U.S. Pat. No. 5,270,163; Tuerk et al. (1990) Science 249:505-510; Szostak et al. (1990) Nature 346:818-822; and Joyce (1989) Gene 82:83-87, which is incorporated by reference in its entirety. An oligonucleotide pool is constructed having two polymerase chain reaction (PCR) primer regions flanking a target-binding region. The target-binding region preferably includes a randomized sequence of nucleotides. The oligonucleotide pool is then contacted with a target molecule under conditions which favor binding of the oligonucleotides to the target molecule. Those oligonucleotides that bind the target molecule are separated from those that do not bind the target molecule, using conventional methods such as filtration, centrifugation, chromatography, or the like. The bound oligonucleotides are then dissociated from the target molecule, and amplified (for example, using PCR) to form a pool of oligonucleotides enriched in sequences that bind to the target molecule. Further rounds of binding, separation, dissociation and amplification are performed until an aptamer with the desired binding affinity, specificity or both is achieved. The final aptamer sequence identified can then be prepared chemically or by in vitro transcription.

It can be desirable to reduce or inhibit inflammation of cardiac tissue in a patient. Because Nourin-1 is an early inflammatory signal, inhibiting Nourin-1 mediated inflammation can be beneficial to a patient. Nourin-1 mediated inflammation can be reduced or inhibited by treating a patient with a Nourin-1 antagonist, a substance that interferes with the Nourin-1 pathway or with Nourin-1 function. One example of a Nourin-1 antagonist is a Nourin-1 antibody, a modified antibody, or a binding region of an antibody. Other examples include a Nourin-1 analog or mimic that can prevent Nourin-1 from exhibiting its biological effect. Such reagents capable of binding, blocking or interfering Nourin-1 inhibit the release of downstream inflammatory signals such as IL-8 (see, for example, U.S. Pat. No. 5,606,027, which is incorporated by reference in its entirety). Thus, administering antibodies that bind to Nourin-1 can be of benefit to a patient in need of preventing, inhibiting, or treating inflammation. In particular, the patient can be in need of preventing, inhibiting, or treating inflammation of cardiac tissue.

EXAMPLES

Serum and plasma samples were collected from six female healthy volunteers aged 20-29, and ten ACS patients. Clinical diagnosis of the ten ACS patients indicated one unstable angina patient and 9 patients with acute myocardial infarction (AMI). The unstable angina patient arrived to the Emergency Department 30.5 hours after symptoms onset. Seven of the nine AMI patients presented to the Emergency Department within 1.5-3.5 hours after onset of chest pain. The other two AMI patients arrived 10 hours and 24 hours after symptoms onset. Blood samples were collected upon arrival of the patient, centrifuged and stored at −70° C. for up to 21 days. Serum and plasma samples were tested for neutrophil chemotactic activity using a modified Boyden chamber technique and human neutrophils as indicator cells (see, for example, Elgebaly, S. A., et al. *J. Mol. Cell. Cardiol.* 21:585-593, 1989; and Elgebaly, S. A., et al. *Am. J. Pathol.* 137:1233-1241, 1990, each of which is incorporated by reference in its entirety).

Samples were also fractionated using high performance liquid chromatography (HPLC) and a size exclusion column (1-300 kDa). The 5 kDa and lower molecular weight fractions were collected and assayed for neutrophil chemotactic activity. The standard synthetic chemoattractant fMet-Leu-Phe (f-MLP) was used as the positive control for 100% chemotactic response. Hank's Balanced Salt Solution (HBSS) was the negative control for random migration. Neutrophil migration was reported as chemotactic index of counted cells trapped within 10-micron membrane layer. The average of three readings were calculated for each filter.

$$\text{Chemotatic Index} = \frac{\text{Patient or Control chemotactic value}}{\text{Mean Normal chemotactic value}}$$

Statistical t-test evaluation was performed using two samples with unequal variance analysis.

Figure 2:
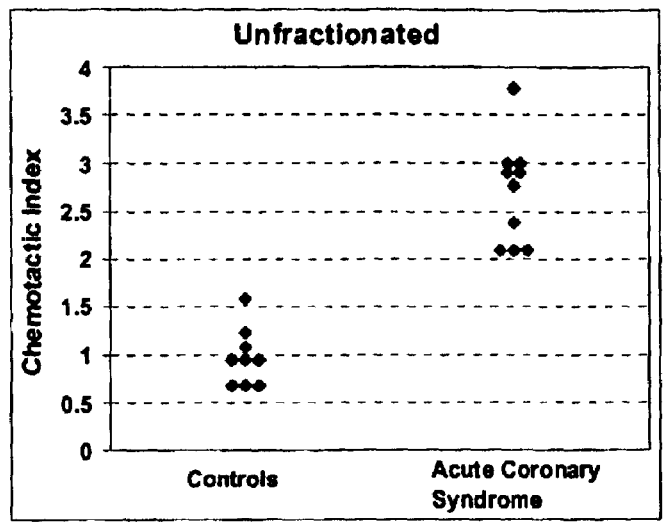
FIG. 2 is a graph depicting neutrophil chemotactic activity of samples taken from acute coronary syndrome patients and from healthy volunteers.
Figure 3:
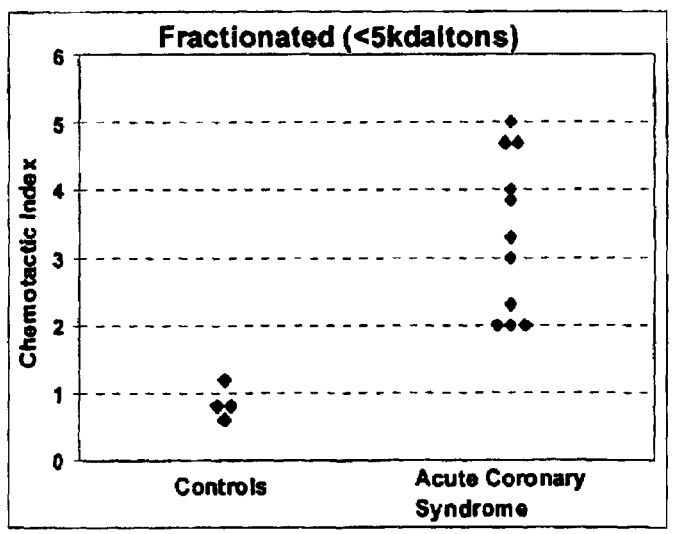
FIG. 3 is a graph depicting neutrophil chemotactic activity of samples taken from acute coronary syndrome patients and from healthy volunteers.

As described in FIGS. 2 and 3, higher levels of neutrophil chemotactic activity were detected in plasma samples of the ten ACS patients than in plasma taken from normal healthy subjects (n=6). In FIG. 2, the chemotactic activity of whole plasma samples taken from ACS patient was 2.70±0.17 (average±standard error), while samples from healthy subjects showed activity of 0.97±0.1 (P value≦0.00001).

As shown in FIG. 3, sub-5 kDa HPLC fractions of plasma samples from ACS patients showed a chemotactic activity of 3.21±0.36 while normal samples showed activity of 0.85±0.12 (P value≦0001). For the UA patient, neutrophil chemotactic activity was detected, despite the absence of an elevated CK-MB level for this patient. Furthermore, Nourin-1 activity was detected in all seven of the nine AMI patients who arrived to the Emergency Department between 1.5 and 3.5 hours after the onset of chest pain. This finding suggests that the cardiac-derived Nourin-1 is an earlier marker for AMI than CK-MB or Troponin I, which are released 4 to 8 hours after the onset of chest pain. In one of these seven AMI patients, Nourin-1 was detected whereas troponin I was absent, supporting the findings that neutrophil chemotactic activity appears significantly earlier than the cardiac marker troponin I.

The neutrophil chemotactic activity of Nourin-1 can be used in the early diagnosis of myocardial ischemia and infarction. Detecting an elevated level of Nourin-1 in a patient can be useful in distinguishing patients who do not initially present elevated levels of traditional markers. For example, a patient suffering cardiac ischemia may have an elevated level of Nourin-1 at the time he or she arrives in the emergency department, but not have elevated levels of CK-MB, troponin I or troponin T for several hours. A medical professional can make treatment decisions based on the results of a patient's Nourin-1 test.

Nourin-1 was isolated from cardioplegic effluents collected during coronary bypass surgery from over 80 human patients. Briefly, Nourin-1 was purified by size exclusion HPLC using a 1-300 kDa column. Fractions corresponding to molecular weights of less than 5 kDa were further resolved by SDS-PAGE, under reducing or non-reducing conditions. Gels were stained with either silver stain or Coomassie blue, and bands of interest (at ~3 kDa and ~6 kDa) cut from the gel. The ~6 kDa band was not apparent under reducing conditions. The resulting gel fragments were washed and subjected to trypsin digestion. The resulting tryptic peptides were extracted from the gel fragments and analyzed by MALDI-MS or nanospray MS/MS. Masses observed in both MS experiments are shown in Table 1. The sequences in Table 1 are the sequences determined by MS/MS for the corresponding mass, detected in both MALDI and MS/MS experiments.

TABLE 1

| # | observed mass (Da) | sequence | calculated pI of sequence |
|---|---|---|---|
| 1 | 1046 | QKPSPSTMR (SEQ ID NO: 1) | 11.51 |
| 2 | 1049 | HALYDEMR (SEQ ID NO: 2) | 5.24 |
| 3 | 1620 | MIINHNLAAINSHR (RESIDUES 1-14 SEQ IS NOS 15-17) | 10.90 |
| 4 | 982 | AQRIGVPSR (SEQ ID NO: 3) | 12.50 |
| 5 | 1320 | MNTRAMNDASGR (SEQ ID NO: 4) | 10.75 |
| 6 | 1122 | LAAQGLDALPR (SEQ ID NO: 5) | 6.8 |
| 7 | 672 | MENHK (SEQ ID NO: 6) | 7.64 |
| 8 | 634 | VGAFKN (SEQ ID NO: 7) | 10.10 |
| 9 | 1612 | SPGADGNGGEAMPGGG (RESIDUES 15-30 SEQ IS NOS 15-17) | |
| 10 | 1141 | GTVGPDVIDIR (SEQ ID NO: 8) | |
| 11 | 1393 | KSQNMALMGGLTK (SEQ ID NO: 9) | |
| 12 | 2906 | ELLHYCLLREIPFFYA (SEQ ID NO: 10) | |
| 13 | 2289 | YAVLCGGGANHRLGLT (SEQ ID NO: 11) | |

TABLE 1-continued

| # | observed mass (Da) | sequence | calculated pI of sequence |
|---|---|---|---|
| 14 | 1279 | MIGTGGFIGASLR (SEQ ID NO: 12) | |
| 15 | 1492 | VGDYVVHVNHGIGK (SEQ ID NO: 13) | |
| 16 | 1492 | VVVGTLDPNPLVSGK (SEQ ID NO: 14) | |

Additional sequences detected by mass spectrometry included: -GSEV- (SEQ ID NO: 18), -VDQPD- (SEQ ID NO: 19) or -VDKPD- (SEQ ID NO: 20), -GTVGPDVIDIR- (SEQ ID NO: 8), -WYLVDASGLVLGRLAV- (SEQ ID NO: 21), and -ADAFVYDAPYNVVAVD- (SEQ ID NO: 22).

The sequences numbered 3 and 9 in Table 1 were chosen as the most likely components of Nourin-1. The combined 3+9 sequence (MIINHNLAAINSHRSPGAD-GNGGEAMPGGG) (SEQ ID NO: 15) has a molecular weight of approximately 3 kDa, consistent with the apparent molecular weight of Nourin-1 determined by SDS-PAGE. The sequence has a predicted pI of 6.02. The same sequence with a C-terminal Lys or Arg residue added has a predicted pI of 7.79 or 7.81, respectively. Nourin-1 has a pI of between 7 and 8. The N-terminal region of the sequence, MII-, shares the Met-hydrophobic-hydrophobic pattern of the chemotactic tripeptide N-formyl-Met-Leu-Phe (fMLP).

A synthetic peptide having the sequence: N-formyl-MI-INHNLAAINSHRSPGADGNGGEAMPGGGK (SEQ ID NO: 16) (i.e., N-formyl-3+9+K, the 3+9 sequence indicated above, where the N-terminus is modified with a formyl group and a lysine has been added to the C-terminus of 9) promoted strong chemotaxis of neutrophils in a modified Boyden chamber assay, as did N-formyl-MIINHNLAAINSHR (RESIDUES 1-14 OF SEQ ID NOS 15-17) (N-formyl-3). Synthetic peptides of sequence: MIINHNLAAINSHR (RESIDUES 1-14 OF SEQ ID NOS 15-17) (i.e., unmodified peptide 3) and of sequence: MIINHNLAAINSHRSPGAD-GNGGEAMPGGG (SEQ ID NO: 15) (unmodified 3+9) promoted chemotaxis to a lesser degree. A synthetic peptide of sequence: SPGADGNGGEAMPGGG (RESIDUES 15-30 OF SEQ ID NOS 15-17) (9) showed no chemotactic activity. Unlike the bacterial chemotactic peptide fMLP, the peptides N-formyl-3+9+K, N-formyl-3, and 3+9 retained chemotactic activity when refrigerated overnight. Synthetic peptides having the sequences: N-formyl-MNTRAMNDASGR (SEQ ID NO: 4) (N-formyl-5) and N-formyl-MENHK (SEQ ID NO: 6) (N-formyl-7) promote chemotaxis to a lesser degree than fMLP, since these peptides lack the N-formyl-Met-hydrophobic-hydrophobic pattern of fMLP.

Other embodiments are within the scope of the following claims.

What is claimed is:

1. An isolated or purified synthetic polypeptide comprising the sequence: N-formyl-MIINHNLAAINSHRSPGAD-GNGGEAMPGGG- (SEQ ID NO: 15), wherein the polypeptide promotes chemotaxis.

2. The polypeptide of claim 1, wherein the polypeptide comprises the sequence N-formyl-MIINHNLAAINSHRSP-GADGNGGEAMPGGGK- (SEQ ID NO: 16).

3. The polypeptide of claim 1, wherein the polypeptide comprises the sequence N-formyl-MIINHNLAAINSHRSP-GADGNGGEAMPGGGR- (SEQ ID NO: 17).

4. The polypeptide of claim 1, wherein the polypeptide has a molecular weight of no greater than 10 kDa.

5. An isolated or purified synthetic polypeptide comprising the sequence: MIINHNLAAINSHRSPGAD-GNGGEAMPGGG (SEQ ID NO: 15), wherein the polypeptide promotes chemotaxis.

6. The polypeptide of claim 5, wherein the polypeptide comprises the sequence MIINHNLAAINSHRSPGAD-GNGGEAMPGGGK (SEQ ID NO:16).

7. The polypeptide of claim 5, wherein the polypeptide comprises the sequence MIINHNLAAINSHRSPGAD-GNGGEAMPGGGR (SEQ ID NO:17).

8. The polypeptide of claim 5, wherein the polypeptide has a molecular weight of no greater than 10 kDa.

9. A method of making an antibody, said method comprising:
   administering to an animal the peptide of claim 1, and
   providing sufficient time for the animal to develop antibodies against the peptide.

10. The method of claim 9, further comprising purifying the antibody.

11. The method of claim 9, further comprising producing a monoclonal antibody that specifically reacts to the peptide.

12. A method of making an antibody, said method comprising:
    administering to an animal the peptide of claim 5, and
    providing sufficient time for the animal to develop antibodies against the peptide.

13. The method of claim 12, further comprising purifying the antibody.

14. The method of claim 12, further comprising producing a monoclonal antibody that specifically reacts to the peptide.

* * * * *

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Lys Pro Ser Pro Ser Thr Met Arg
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ala Leu Tyr Asp Glu Met Arg
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Ala Gln Arg Ile Gly Val Pro Ser Arg
 1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Asn Thr Arg Ala Met Asn Asp Ala Ser Gly Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Ala Gln Gly Leu Asp Ala Leu Pro Arg
 1               5                  10

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Glu Asn His Lys
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Gly Ala Phe Lys Asn
 1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Thr Val Gly Pro Asp Val Ile Asp Ile Arg
 1               5                  10

<210> SEQ ID NO 9
<211> LENGTH: 13
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 9

Lys Ser Gln Asn Met Ala Leu Met Gly Gly Leu Thr Lys
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Leu Leu His Tyr Cys Leu Leu Arg Glu Ile Pro Phe Phe Tyr Ala
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ala Val Leu Cys Gly Gly Gly Ala Asn His Arg Leu Gly Leu Thr
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Ile Gly Thr Gly Gly Phe Ile Gly Ala Ser Leu Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Gly Asp Tyr Val Val His Val Asn His Gly Ile Gly Lys
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Val Val Gly Thr Leu Asp Pro Asn Pro Leu Val Ser Gly Lys
1               5                   10                  15

```
<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Ile Ile Asn His Asn Leu Ala Ala Ile Asn Ser His Arg Ser Pro
 1               5                  10                  15

Gly Ala Asp Gly Asn Gly Gly Glu Ala Met Pro Gly Gly Gly
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Ile Ile Asn His Asn Leu Ala Ala Ile Asn Ser His Arg Ser Pro
 1               5                  10                  15

Gly Ala Asp Gly Asn Gly Gly Glu Ala Met Pro Gly Gly Gly Lys
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Ile Ile Asn His Asn Leu Ala Ala Ile Asn Ser His Arg Ser Pro
 1               5                  10                  15

Gly Ala Asp Gly Asn Gly Gly Glu Ala Met Pro Gly Gly Gly Arg
            20                  25                  30

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Glu Val
 1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Asp Gln Pro Asp
 1               5
```

```
<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Asp Lys Pro Asp
 1               5

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Tyr Leu Val Asp Ala Ser Gly Leu Val Leu Gly Arg Leu Ala Val
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Asp Ala Phe Val Tyr Asp Ala Pro Tyr Asn Val Val Ala Val Asp
 1               5                  10                  15
```